US009451831B2

(12) United States Patent
Richardson et al.

(10) Patent No.: US 9,451,831 B2
(45) Date of Patent: *Sep. 27, 2016

(54) TATTOO STOOL OR A CHAIR (71) Applicant: InkBed, Inc., Everett, WA (US)

(72) Inventors: Kevin Richardson, Everett, WA (US);
Edgar Zavala, Chicago, IL (US)

(73) Assignee: InkBed, Inc., Everett, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/791,110

(22) Filed: Jul. 2, 2015

(65) Prior Publication Data
US 2015/0305508 A1 Oct. 29, 2015

Related U.S. Application Data

(63) Continuation of application No. 14/151,753, filed on Jan. 9, 2014, now Pat. No. 9,084,486.

(51) Int. Cl.
*A47C 9/00* (2006.01)
*A47C 25/00* (2006.01)
(Continued)

(52) U.S. Cl.
CPC . *A47C 9/00* (2013.01); *A47C 3/00* (2013.01); *A47C 7/00* (2013.01); *A47C 7/54* (2013.01); *A47C 7/543* (2013.01); *A47C 9/02* (2013.01); *A47C 13/00* (2013.01); *A47C 15/004* (2013.01); *A61G 15/007* (2013.01); *A61G 15/12* (2013.01); *A61M 37/0076* (2013.01); *A47C 1/11* (2013.01);
(Continued)

(58) Field of Classification Search
CPC ........ A47C 7/54; A47C 1/11; A47C 15/004; A47C 9/005; A47C 9/02; A61G 15/007; A61B 19/28

USPC .............. 297/195.11, 461, 462, 344.21, 201, 297/312, 423.1, 423.11, 423.12, 423.19, 297/423.22, 423.25, 423.26, 411.37, 297/411.31, 411.35
See application file for complete search history.

(56) References Cited

U.S. PATENT DOCUMENTS 3,145,053 A  *  8/1964  Thompson et al. .......... 297/383
3,188,136 A       6/1965  Redfield et al.
(Continued)

FOREIGN PATENT DOCUMENTS

CN          2151738 Y        1/1994
CN        201119969 Y        9/2008
(Continued)

OTHER PUBLICATIONS

International Searching Authority, International Search Report and Written Opinion, PCT Patent Application PCT/US2015/010910, mailed May 11, 2015, 14 pages.
(Continued)

*Primary Examiner* — Chi Q Nguyen
(74) *Attorney, Agent, or Firm* — Perkins Coie LLP (57) ABSTRACT

An apparatus that supports a tattoo artist in a variety of positions to comfortably apply one or more tattoos to skin of a subject is herein disclosed. The apparatus can be reconfigured to optimally position and support the arms and/or chest of the tattoo artist. A method for using a tattoo stool can involve rotating armrests of the apparatus from a stowed position to a deployed position. The armrests can support the user's forearms while supporting the user's chest such that the user can comfortably tattoo a portion of the subject positioned in front of the stool.

15 Claims, 6 Drawing Sheets

(51) Int. Cl.

| | | |
|---|---|---|
| *A47C 7/54* | (2006.01) | |
| *A47C 15/00* | (2006.01) | |
| *A47C 9/02* | (2006.01) | |
| *A61G 15/00* | (2006.01) | |
| *A61G 15/12* | (2006.01) | |
| *A61M 37/00* | (2006.01) | |
| *A47C 13/00* | (2006.01) | |
| *A47C 3/00* | (2006.01) | |
| *A47C 7/00* | (2006.01) | |
| *A47C 1/11* | (2006.01) | |
| *A61B 19/00* | (2006.01) | |
| *A61G 13/12* | (2006.01) | |

(52) U.S. Cl.
CPC ............... *A47C 9/005* (2013.01); *A61B 19/28* (2013.01); *A61B 90/60* (2016.02); *A61G 13/122* (2013.01); *A61G 13/1235* (2013.01)

(56) References Cited

U.S. PATENT DOCUMENTS

| | | | |
|---|---|---|---|
| 3,227,440 A | | 1/1966 | Scott |
| 4,170,800 A | | 10/1979 | Wiberg |
| 4,285,541 A | | 8/1981 | Onishi |
| 4,387,888 A | | 6/1983 | Marinakis |
| 4,516,805 A | | 5/1985 | Leeper et al. |
| 4,650,249 A | * | 3/1987 | Serber .................. 297/313 |
| 4,660,549 A | | 4/1987 | Kowalski et al. |
| 4,795,214 A | | 1/1989 | Holdt |
| 5,060,327 A | | 10/1991 | Celestina et al. |
| 5,086,769 A | | 2/1992 | Vianello et al. |
| 5,098,158 A | | 3/1992 | Palarski |
| 5,315,722 A | | 5/1994 | Djie |
| 5,401,078 A | * | 3/1995 | Riach .................. 297/423.11 |
| 5,487,590 A | * | 1/1996 | Haynes .................. 297/344.14 |
| 5,642,542 A | | 7/1997 | Kometani |
| 5,645,313 A | | 7/1997 | Best et al. |
| 5,653,499 A | | 8/1997 | Goodall |
| 5,678,894 A | | 10/1997 | Eley |
| 5,762,402 A | * | 6/1998 | Gillotti .................. 297/423.11 |
| 5,967,610 A | * | 10/1999 | Lin .................. 297/340 |
| 5,971,475 A | | 10/1999 | Lawson et al. |
| 5,971,485 A | * | 10/1999 | Clark .................. 297/423.12 |
| 6,089,593 A | | 7/2000 | Hanson et al. |
| 6,135,548 A | | 10/2000 | McGuire |
| 6,212,713 B1 | | 4/2001 | Kuck et al. |
| 6,315,319 B1 | | 11/2001 | Hanson et al. |
| 6,446,287 B2 | | 9/2002 | Borders |
| 6,619,747 B2 | * | 9/2003 | Ko et al. .................. 297/423.12 |
| 6,767,066 B1 | | 7/2004 | Tornero |
| 6,824,219 B2 | | 11/2004 | Ruckstadter |
| 6,846,042 B2 | | 1/2005 | Hanson et al. |
| 6,918,143 B2 | | 7/2005 | Wiberg |
| 7,021,037 B1 | * | 4/2006 | Szymas .................. 54/44.1 |
| 7,080,885 B2 | * | 7/2006 | Bain et al. .................. 297/354.1 |
| 7,234,768 B2 | * | 6/2007 | Manning .................. 297/94 |
| 7,293,834 B2 | | 11/2007 | Riach et al. |
| 7,600,817 B2 | | 10/2009 | Kramer et al. |
| 7,784,871 B2 | | 8/2010 | Cochran et al. |
| 8,651,569 B2 | | 2/2014 | Andoloro et al. |
| 9,084,486 B1 | | 7/2015 | Richardson et al. |
| 2002/0000008 A1 | | 1/2002 | Borders |
| 2002/0067060 A1 | * | 6/2002 | Lloyd .................. 297/195.11 |
| 2004/0133979 A1 | | 7/2004 | Newkirk et al. |
| 2006/0225212 A1 | | 10/2006 | Parson et al. |
| 2007/0052275 A1 | * | 3/2007 | Ghilzai .................. 297/423.12 |
| 2009/0250565 A1 | | 10/2009 | Jaggers et al. |
| 2010/0295357 A1 | | 11/2010 | Koehler et al. |
| 2011/0272976 A1 | | 11/2011 | Wei et al. |

FOREIGN PATENT DOCUMENTS

| | | |
|---|---|---|
| WO | 2009056004 | 5/2009 |
| WO | 2013078569 A1 | 6/2013 |

OTHER PUBLICATIONS

"Hydraulic All Purpose Tattoo Chair KI New York", http://www.puretat.com, accessed Jan. 18, 2010, 2 pages.

"Tatsoul 370" http://www.tatsoul.com, accessed Feb. 2, 2010, 7 pages.

"Tattoo-Chairs-table", http://www.tattoochair.com, © 2009, accessed Jan. 18, 2010, 7 pages.

"Traveler—The Ultimate Table", http://www.tattootable.com, Fab Tech, accessed Jan. 18, 2010, 3 pages.

\* cited by examiner

TATTOO STOOL OR A CHAIR

CROSS-REFERENCE TO RELATED APPLICATION

This application is a continuation application of U.S. patent application Ser. No. 14/151,753, filed on Jan. 9, 2014, now U.S. Pat. No. 9,084,486, and entitled "TATTOO STOOLS AND CHAIRS AND METHODS USING THE SAME," which is hereby incorporated herein in its entirety by reference.

TECHNICAL FIELD

The present technology is related to support apparatuses for tattoo parlors and associated methods of using the same. In particular, the present technology is related to tattoo stools and tattoo chairs.

BACKGROUND

In tattoo parlors, tattoo artists often sit on stools or chairs while applying tattoos. Conventional stools and chairs are not ergonomically designed for tattoo artists and are not comfortable when, for example, applying relatively large tattoos. For example, a tattoo artist's arms and shoulders can experience significant fatigue when leaning forward to apply a tattoo. Additionally, if a tattoo artist leans forward for a significant period of time, the artist's lower back may experience fatigue and discomfort. Accordingly, there is a need for stools or chairs that can help tattoo artists comfortably apply tattoos to different parts of a subject's body.

SUMMARY OF TECHNOLOGY

An exemplary embodiment is a support apparatus for supporting a tattoo artist. The apparatus can place the tattoo artist's body in ergonomic positions to help reduce or limit fatigue (e.g., muscle fatigue in the artist's arms, shoulders, back, etc.), discomfort, and/or pain. The tattoo artist can straddle the apparatus and can lean forward against a padded chest support. The padded chest support can be narrower than the artist's chest to provide unrestricted movement of the artist's arms on the front side of the chest support. The apparatus can have armrests that are shorter than the artist's forearms to provide unrestricted movement of the artist's hands while the artist's forearms rest on the armrests. The support apparatus can be a stool, a chair, or other reconfigured equipment capable of placing the artist's body in different ergonomic positions. The support apparatus can also be used by a client (i.e., person obtaining a tattoo) and in other settings.

In one embodiments, the apparatus can support a tattoo artist in a variety of positions to comfortably apply one or more tattoos to skin of a client. The apparatus can be a tool stool that is reconfigurable to optimally position and support the arms and/or chest of the tattoo artist. A method for using a tattoo stool can involve rotating armrests of the apparatus from a stowed position for supporting the tattoos artist's arms to a deployed position for supporting the tattoo artist's arms. The armrests can support the user's forearms while supporting the user's chest such that the artist can comfortably tattoo a body part of the subject positioned in front of the tattoo stool.

In some embodiments, a stool comprises a seat assembly and a chest support assembly. The chest support assembly can include a padded chest support and at least one armrest moveable between a stowed position and a deployed position. The chest support is configured to support the chest of a tattoo artist sitting on the seat assembly while allowing movement to the artist's arms on a front side of the chest support. The armrest, in the deployed position, can extend away from the chest support such that the artist's arm is capable of resting on the portion of the armrest located in front of the chest support. The artist can adjust the configuration of the stool any number of times during a tattoo session. The seat assembly, in some embodiments, includes a seat, a pedestal, hydraulics, mechanisms (e.g., locking mechanisms, tilt adjustment mechanisms, etc.) and/or a plurality of wheels for rolling along a support surface. When the artist straddles the stool (e.g., straddles a vertical support of the chest assembly), the artist can conveniently wheel the stool along the support surface. The seat assembly can include a swiveling padded seat to permit convenient rotation of the padded seat. In the stowed position, the armrest can be positioned alongside the chest support. In the deployed position, an elongated main body of the armrest can extend substantially perpendicular to the chest support. However, the armrest can be located at other orientations.

In some embodiments, a support apparatus comprises a seat assembly, a chest support, and an armrest. The chest support can be carried by the seat assembly and is positioned to contact a user's chest while the user sits on the seat assembly. An end of the armrest moves away from the user's chest when the armrest rotates from a raised position to a lowered position. In the raised position, the armrest can support the user's chest for enhanced comfort. In the fully lowered position, the armrest can be positioned to support a user's forearm. For example, the lowered armrest can be oriented horizontally. The end of the lowered armrest and seat assembly can be positioned on opposite sides of a chest pad of the chest support. In some embodiments, most of the length of the armrest (e.g., 70%, 80%, 90%, or 95% of the total length of the armrest) and most of the seat are located on opposite sides of an imaginary vertical plane (e.g., a vertical plane positioned along the chest support).

The support apparatus, in some embodiments, can include a pair of armrests rotatably coupled to opposing sides of the chest support. In one embodiment, the armrests rotate together relative to the chest support. In other embodiments, the armrests are independently rotatable relative to the chest support. For example, a pivoting mechanism can rotatably couple one armrest to the left side of the chest support, and another pivoting mechanism can rotatably couple the other armrest to the right side of the chest support. The pivoting mechanisms can have different states of operation, such as a locked state and an unlocked state.

In further embodiments, a support apparatus can comprise a seat assembly, means for supporting the chest of a user, and means for supporting the user's arm. The seat assembly can carry the means for supporting the chest of the user. The means for supporting the user's arm can support a user's arm while the user sits on the seat assembly and the user's chest rests against the means for supporting the user's chest. In one embodiment, the means for supporting the user's chest includes a padded chest support and a vertical rod, which couples the padded chest support to the seat assembly. The means for supporting the user's arm can include one or more rotatable armrests. The armrests can be padded for enhanced comfort.

In yet further embodiments, a method for using a stool is provided. The method comprises rotating at least one armrest of the stool from a stowed position to a lowered position. A tattoo artist can tattoo at least a portion of a subject (e.g., a client) while the lowered armrest supports the artist's arm and also while the artist's chest rests against a chest support of the stool. In other embodiments, the client can sit on the stool. The client's arm can rest on the armrest while it is tattooed. In other embodiments, the method can be performed using a chair that includes a chest support and armrests.

DETAILED DESCRIPTION

Figure 1:
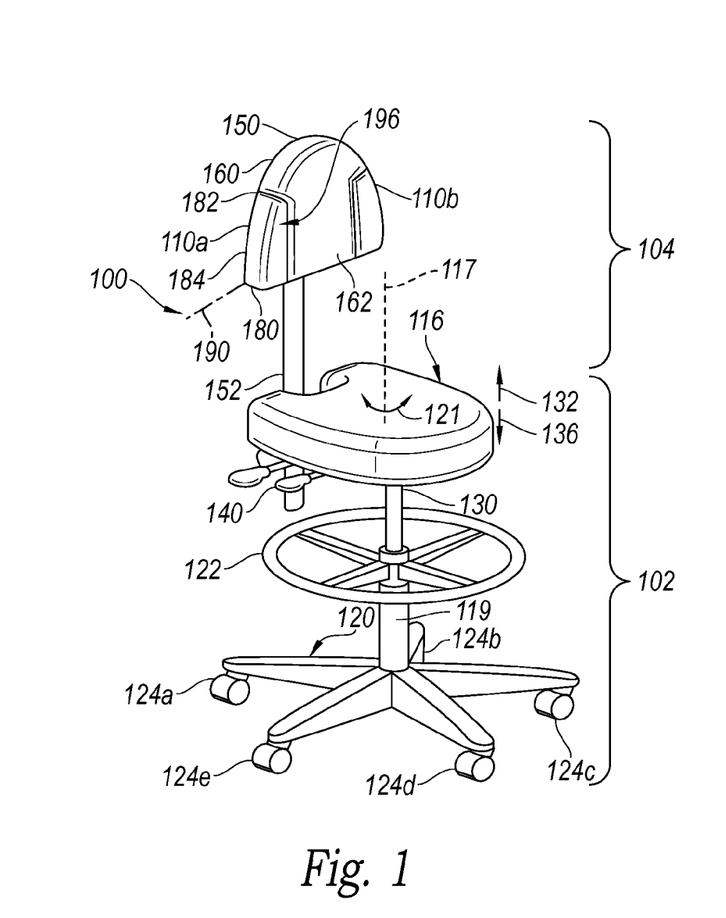
FIG. 1 is an isometric view of a stool with raised armrests in accordance with an embodiment of the present technology.
Figure 2:
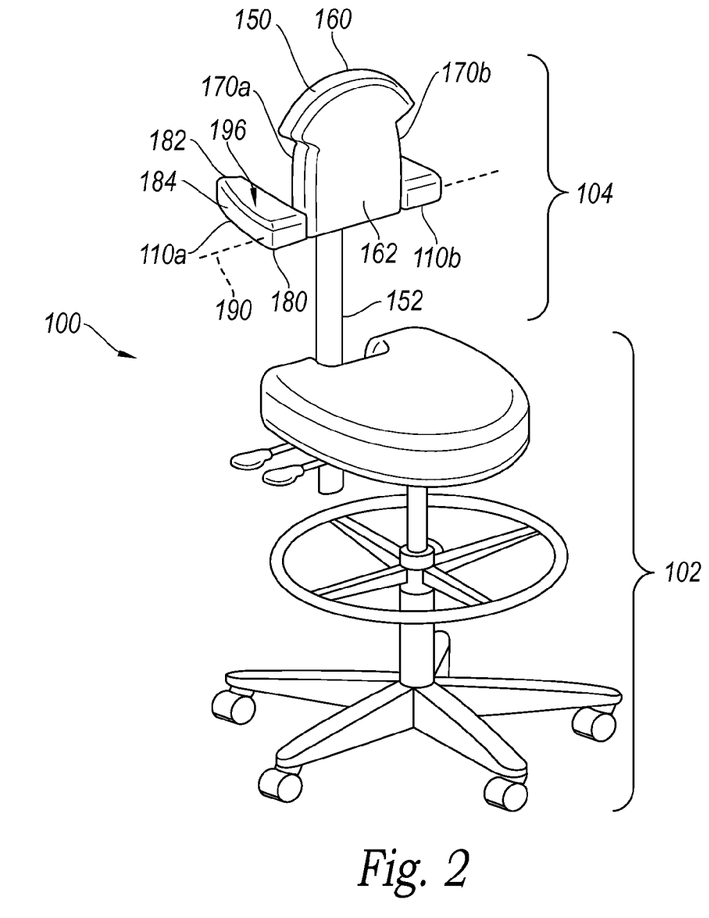
FIG. 2 is an isometric view of the stool of FIG. 1 with lowered armrests.

FIG. 1 is an isometric view of a stool 100 in accordance with an embodiment of the present technology. The stool 100 can include a seat assembly 102 and a chest support assembly 104. A tattoo artist ("artist") can sit on the seat assembly 102 such that the artist's chest rests against the chest support assembly 104. The chest support assembly 104 can help position the artist's upper body and can include armrests 110a, 110b (collectively "armrests 110") movable between stowed or raised positions (FIG. 1) and lowered or deployed positions (FIG. 2). The raised armrests 110 of FIG. 1 are positioned to contact and support the artist's chest whereas the lowered armrests 110 of FIG. 2 can support the tattoo artist's forearms. During a tattoo session, the armrests 110 can be raised and lowered any number of times to tattoo different parts of a person's body.

FIG. 1 shows the seat assembly 102 including a seat 116 and a base assembly 120. The seat 116 can be padded for comfortable sitting. The base assembly 120 can include a base member 119, a foot rest 122, and wheels 124a, 124b, 124c, 124d, 124e (collectively "wheels 124"). The base member 119 can include a hydraulic assembly 130 used to raise (indicated by arrow 132) and lower (indicated by arrow 136) the seat 116. The hydraulic assembly 130 can include a bearing mount or pivot that allows rotation (indicated by arrow 121) of the seat 116 about a vertical axis of rotation 117. A control element in the form of a lever 140 can be used to lower the seat 116. The foot rest 122 can be a ring fixedly coupled to the hydraulic assembly 130 or other component of the base member 119. The wheels 126 can be casters configured to roll along a support surface. The base assembly 120 can have other configurations that provide desired functionality.

Referring to FIG. 2, chest support assembly 104 can include a chest support 150 and an elongate member 152. The chest support 150 has a front side 160 for facing a person to be tattooed and a backside 162 facing the tattoo artist. The chest support 150 can include armrest-receiving portions 170a, 170b having a complementary shape with the armrests 110a, 110b, respectively. When the armrests 110 are in the stowed position (FIG. 1), the armrests 110a, 110b can be received by the armrest-receiving portions 170a, 170b, respectively, such that the chest support assembly 104 (i.e., the chest support 150 and armrests 110) has an upside down U-shape configuration. The size and configuration of the chest support assembly 104 can be selected based on the desired amount of cushion, size of the user, and/or desired range of motion of the tattoo artist.

The armrests 110a, 110b can be generally similar to each other, and accordingly, the description of one armrest 110a, 110b applies equal to the other armrest 110a, 110b, unless indicated otherwise. The armrest 110a can include a mounting end 180, a terminal end 182, and an elongated main body 184 therebetween. The mounting end 180 can be pivotally coupled to the chest support 150. The elongated main body 184 can have an upper surface 196 upon which the artist's arm can rest. A rod (not shown) within the chest support 150 can couple the armrests 110a, 110b together. As such, the armrests 110 can rotate together about an axis of rotation 190. In other embodiments, the armrests 110 are independently rotatable about the axis of rotation 190. For example, one armrest 110 can be in the stowed position while the other armrest 110 can be in the deployed position. The axis of rotation 190 can be a horizontally oriented axis for up and down rotation of the armrests 110, but the axis of rotation 190 can be other orientations.

Figure 3:
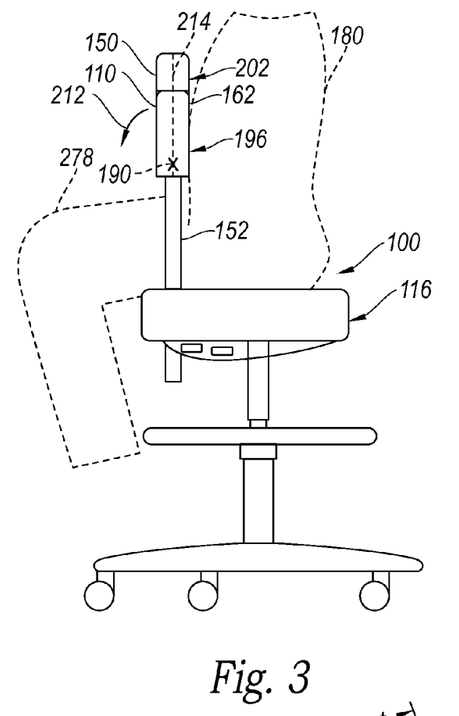
FIG. 3 is a side view of the stool of FIG. 1 with raised armrests and a tattoo artist sitting on the stool.
Figure 4:
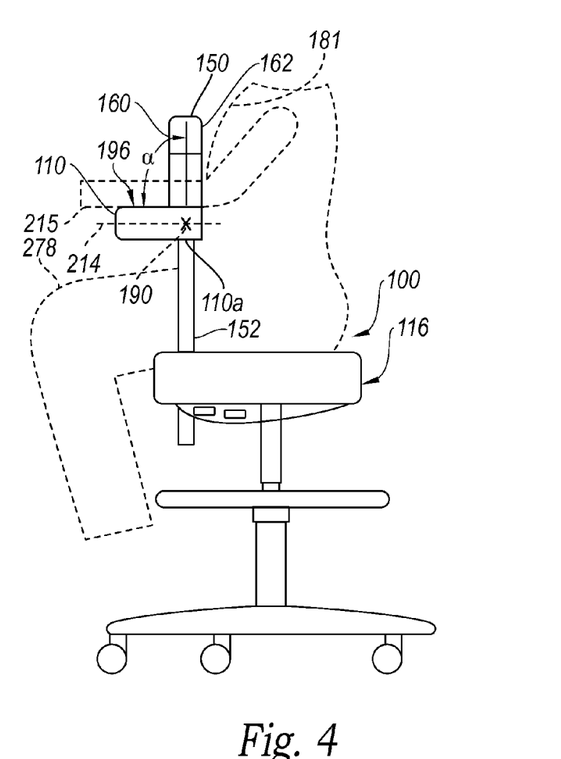
FIG. 4 is a side view of the stool of FIG. 1 with lowered armrests and the tattoo artist sitting on the stool.

FIG. 3 is a side view of the stool 100 with raised armrests 110. FIG. 4 is a side view of the stool 100 with lowered armrests 110. Referring now to FIG. 3, the stowed armrest 110 can be at an upright or substantially vertical orientation. As used herein, the term "substantially vertical" refers to ranges of small angles from vertical, for example, angles between about 0 degrees and 10 degrees from vertical, such as angles less than about 5 degrees, for example, angles less than about 2.5 degrees. The upper surface 196 can be approximately flush with a surface 202 of the chest support 150, illustrated in a substantially vertical orientation. The chest support 150 and the armrests 110 provide a relatively large surface area for contacting the artist's chest.

Referring to FIGS. 3 and 4, the armrest 110 can rotate (indicated by arrow 212 in FIG. 3) about the axis of rotation 190 an angle α (FIG. 4). In some embodiments, the angle α (FIG. 4) can be about 70 degrees to about 100 degrees. In one embodiment, the armrest 110a is rotatable along an arc of about 80 degrees to about 90 degrees. In one embodiment, the angle α is about 90 degrees. The armrest 110 can be rotated from an upright position in which a longitudinal axis 214 of the armrest 110a is substantially vertical (FIG. 3) to the fully deployed position in which the longitudinal axis 214 is substantially horizontal (FIG. 4). As used herein, the term "substantially horizontal" refers to ranges of small angles from horizontal, for example, angles between about 0 degree and 10 degrees from horizontal, such as angles less than about 5 degrees, for example, angles less than about 2.5 degrees. In other embodiments, the fully lowered armrest 110 can be located at other orientations, such as a declined orientation, selected based on the desired body position of the artist.

Referring to FIG. 4, the armrest 110 can extend substantially perpendicular to the vertically oriented chest support 150 and away from the user's torso during use. The user's chest 181 (illustrated in phantom line) can contact the backside 162 of the chest support 150, and the artist's arm 215 can rest on the armrest 110, which extends outwardly on the front side 160 of the chest support 150. The armrest 110 can be shorter than the artist's forearm to provide unrestricted movement of the artist's hand. In some embodiments, the length of the armrest 110 is in a range of about 5 inches (12.7 cm) to about 1 ft. (30.5 cm), but other lengths can be selected based on, for example, the length of the artist's forearm. If the stool 100 is used by a client, longer armrests can be used to support the client's forearm and hand. As shown in FIG. 4, the artist's leg 278 can be positioned generally underneath the armrest 110 to help keep the artist's body properly aligned with the chest support 150. The artist's arm 215 can freely move to tattoo a subject located in front of the stool 100 while the chest support 150 comfortably supports the artist's chest/stomach 181 to reduce, limit, or substantially eliminate fatigue (e.g., muscle fatigue in the artist's arms, shoulders, and/or back), discomfort, and/or pain.

Figure 5:
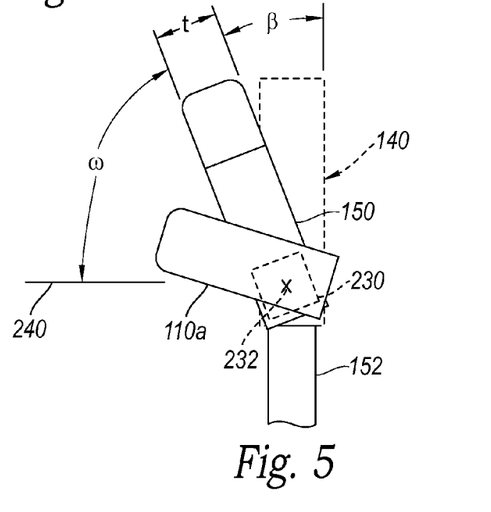
FIG. 5 is a side view of a chest support in different positions in accordance with an embodiment of the present technology.

The chest support 150 can be rotationally fixed to the elongate member 152 and can remain in a substantially vertical orientation during use. In some embodiments, the chest support 150 can be rotated relative to the elongate member 152 for enhanced comfort. FIG. 5 is a side view of the chest support 150 rotated in accordance with an embodiment of the present technology. A pivoting or tilt mechanism 230 (illustrated in phantom line) has an unlocked state and a locked state. In the unlocked state, the pivoting mechanism 230 allows rotation of the chest support 150 about an axis of rotation 232 to move the chest support 150 between a first orientation (e.g., a vertical orientation) to another orientation (e.g., a non-vertical orientation). The axis of rotation 232 can be aligned with the axis of rotation 190 (FIGS. 2 and 3). For example, the axis of rotation 232 can be parallel to the axis of rotation 190. However, the axes of rotation 190, 232 can be at other orientations.

The pivoting mechanism 230 can include, without limitation, one or more release mechanisms, hinges, bearings, pins, or combinations thereof and may be capable of manual locking and unlocking. In the locked state, the pivoting mechanism 230 inhibits or prevents rotation of the chest support 150 about the axis of rotation 232. In the unlocked state, the chest support 150 can be rotated about the axis of rotation 232 an angle of rotation β equal to or less than a maximum angle, such as about 70 degrees, 80 degrees, or 90 degrees. In push-button embodiments, the pivoting mechanism 230 can include a button that can be depressed to switch the state of the pivoting mechanism 230. The configuration and operation of the pivoting mechanism 230 can be selected based on the desired reconfigurability of the stool 100. Pivoting mechanisms can also be incorporated into armrests, and in certain embodiments, such pivoting mechanisms can lock armrests at multiple orientations (e.g., a declined orientation, a horizontal orientation, an inclined orientation, a vertical orientation, etc.).

The chest support 150 can be positioned at different angles of inclination ω (i.e., the angle defined by the chest support 150 and a generally horizontal imaginary plane 240). In some embodiments, the angle of inclination ω is equal to or greater than about 30 degrees, 40 degrees, 50 degrees, 60 degrees, 70 degrees, 80 degrees, or 85 degrees. In particular embodiments, the angle of inclination ω is in a range of about 45 degree to about 90 degrees. The artist can reposition the chest support 150 at any time during the tattoo session to minimize, limit, or substantially eliminate fatigue discomfort and/or pain. If the artist has to lean over for a significant length of time, the inclination of the chest support 150 can be varied as desired. The armrest 110a (or armrest 110b) can be locked at a desired position relative to the inclined chest support 150. For example, the angle of inclination ω can be about 45 degrees while one or both armrests 110 are substantially horizontal. The chest support 150 and armrests 110 can be conveniently repositioned any number of times during a single tattoo session.

Figure 6:
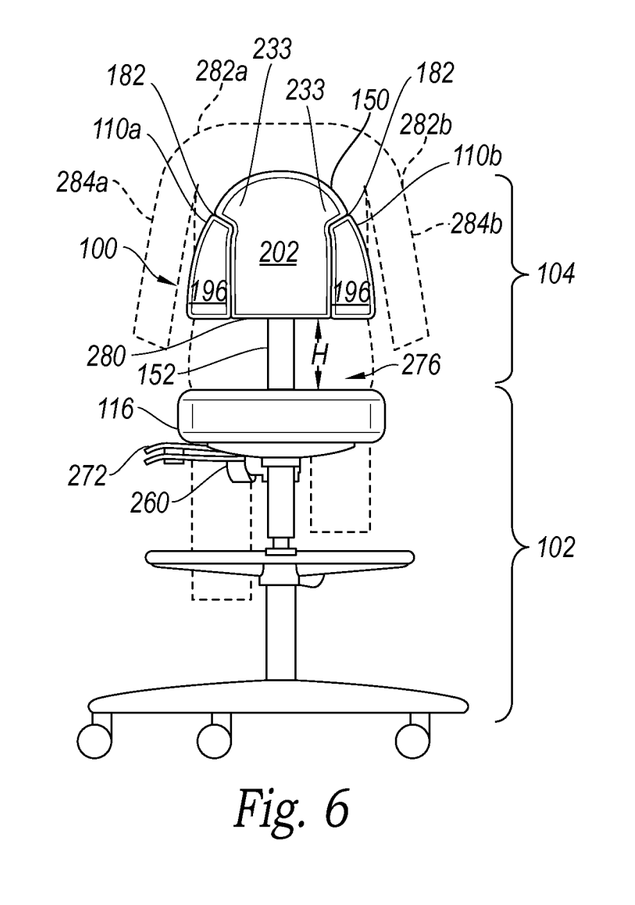
FIGS. 6 and 7 are back views of the stool of FIG. 1.
Figure 7:
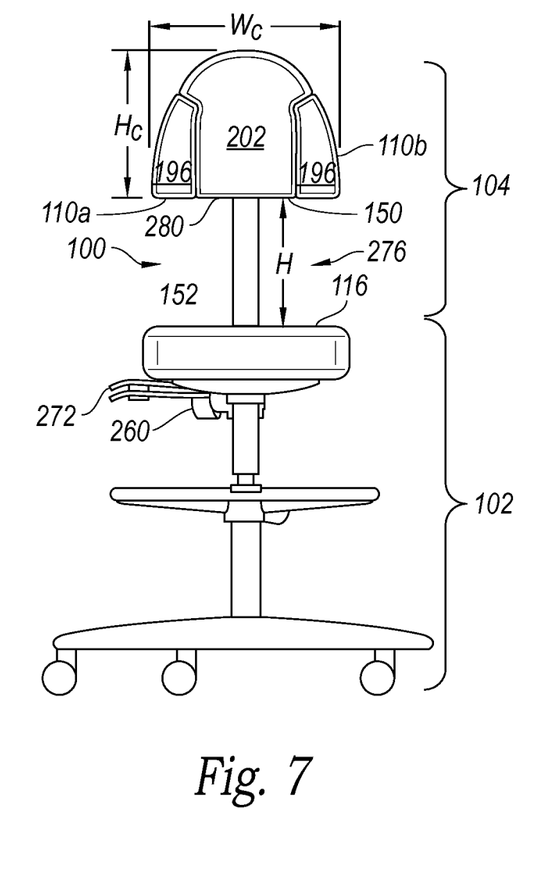

FIG. 6 is a back view of the stool 100 with the chest support 150 at a lowered position. FIG. 7 is a back view of the stool 100 with the chest support 150 at a raised position. The stool 100 can include a vertical adjustment mechanism 260 coupling the elongate member 152 to the seat assembly 102. A user can operate a control element 272 (illustrated as a lever) to switch the adjustment mechanism 260 between a locked state and an unlocked state. In the unlocked state, the adjustment mechanism 260 allows vertical movement of chest support 150 relative to the seat 116 to adjust a height H of a leg-receiving gap 276. In the locked state, the adjustment mechanism 260 can prevent vertical movement of the chest support 150. When the artist straddles the elongate member 152, the artist's legs can be positioned in the leg-receiving gap 276 and securely held between a bottom 280 of the chest support 150 and the seat 116.

FIG. 6 shows the chest support assembly 104 overlaying a user's chest. Laterally-extending side portions or wings 233 ("side portions 233") of the chest support 150 can extend across most or substantially all the width of the armrest ends 182. In some embodiments, at least about ¼, ½, or ¾ of the width of each armrest 196 is positioned directly underneath respective side portions 233. As shown in FIG. 6, the armrests 196 can be positioned vertically between the side portions 233 and the seat 116. However, the armrests 196 can be at other orientations and have other configurations.

The user's shoulders 282a, 282b can be spaced apart from the chest support 150 and armrests 110 to permit free movement of the user's arms 284a, 284b. In some embodiments, the chest support assembly 104 is generally narrower than the width of the user's torso such that the artist can move their elbows along their sides without contacting the chest support assembly 104. In some embodiments, a height $H_C$ (FIG. 7) of the chest support 150 can be in a range of about 5 inches (12.7 cm) to about 1 ft. (30.5 cm). The width $W_C$ (FIG. 7) of the chest support assembly 104 can be in a range of about 8 inches (20.3 cm) to about 1 ft. (30.5 cm). As such, the chest support assembly 104 can be narrower than the tattoo artist's chest to provide generally unrestricted movement of the tattoo artist's arms on the front side of the stool 100. In one embodiment, the chest support 150 and armrests 110 are dimensioned to overlay the chest of the tattoo artist such that most of the surfaces 196, 202 contact the artist's chest. The thickness t (FIG. 5) of the chest support 150 and/or armrests 110 can be in a range of about 0.5 inch (1.3 cm) to 2 inches (5 cm). The dimensions of the components of the chest support assembly 104 can be selected based on, for example, the size of the tattoo artist, desired amount of support, and/or type of tattooing to be performed. Accordingly, other dimensions can be used, if needed or desired.

Figure 8:
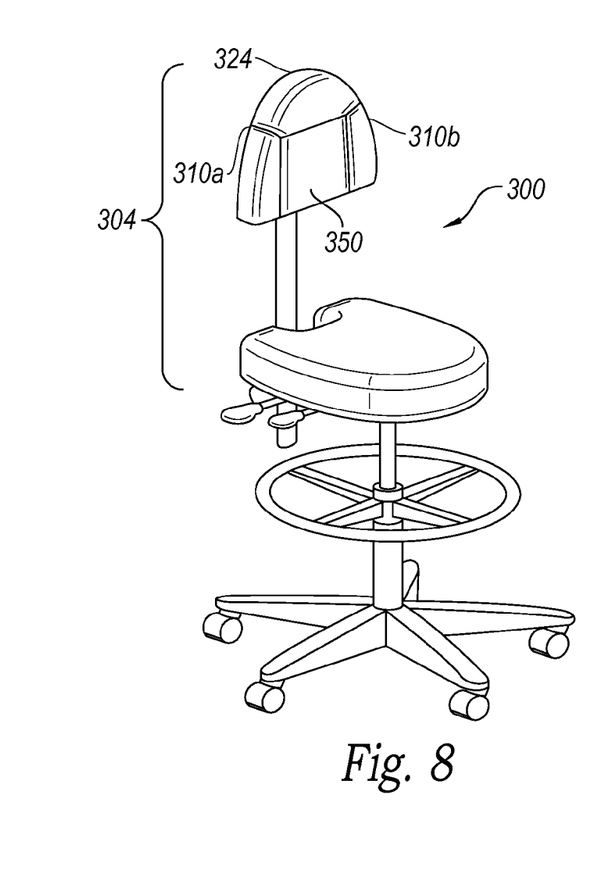
FIG. 8 is an isometric view of a stool with raised armrests in accordance with an embodiment of the present technology.
Figure 9:
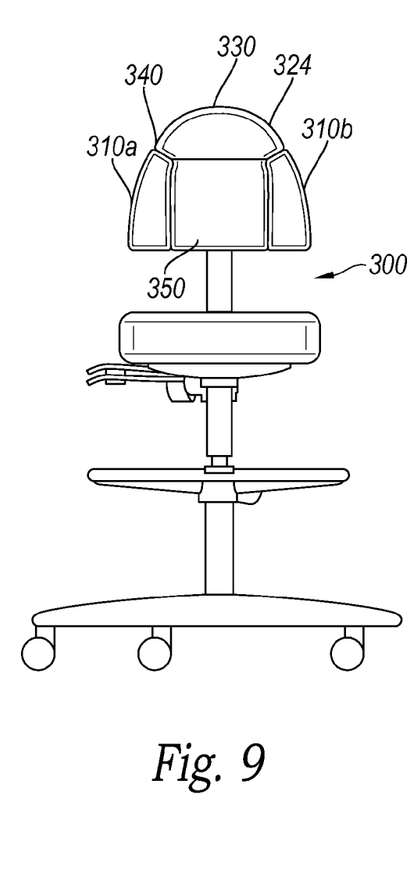
FIG. 9 is a back view of the stool of FIG. 8.
Figure 10:
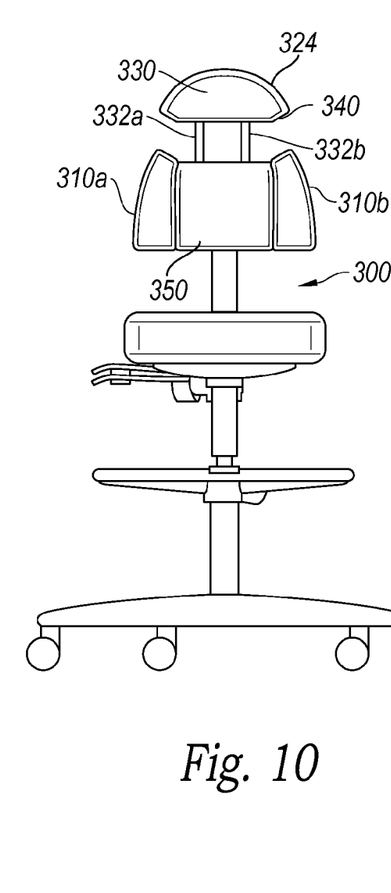
FIG. 10 is a back view of the stool of FIG. 8 with an upper chest support in a raised position.

FIG. 8 is an isometric view of a stool 300 in accordance with an embodiment of the present disclosure. The description of the stool 100 discussed in connection with FIGS. 1 to 7 applies equally to the stool 300, except as detailed below. The stool 300 can include a chest support assembly 304 with armrests 310a, 310b, a chest support 350, and an upper chest support member 324 ("upper support member 324"). The upper support member 324 is moveable between a lowered position (FIGS. 8 and 9) and a raised position (FIG. 10). The armrests 310 can be raised and lowered independent of the position of the upper support member 324.

Referring to FIG. 10, the upper support member 324 can include a main body 330 and a pair of rods 332a, 332b (collectively "rods 332"). The main body 330 can be padded and can include a lower portion 340 configured to mate with the armrests 310a, 310b and the chest support 350. The chest support 350 can have a generally square shape (shown in FIGS. 9 and 10) or rectangular shape, but it can have other configurations. When the upper support member 324 is in the lowered position (FIG. 9), the rods 332 can be positioned within the chest support 350. A user can lift upwardly on the main body 330 to raise the support member 324 relative to the chest support 350. The rods 332 can extend from the chest support 350 until the upper support member 324 is at the desired height. In some embodiments, a locking mechanism can be used to lock and unlock the upper support member 324.

Figure 11:
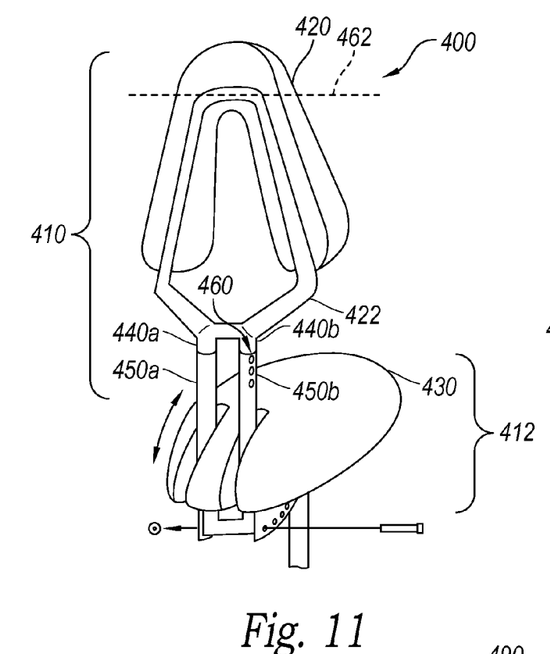
FIG. 11 is an isometric view of a chest support assembly in accordance with an embodiment of the present technology.

FIG. 11 is an isometric view of a portion of a stool 400 in accordance with an embodiment of the present technology. The stool 400 can include a chest support assembly 410 and a seat assembly 412. The chest support assembly 410 can include a chest support 420 and a frame 422, which couples the chest support 420 to a seat 430. The chest support 420 can have an upside down V-shape or U-shape. The frame 422 can be fixedly coupled to the chest support 420 by, for example, one or more brackets, fasteners (e.g., screws, nut and bolt assembles, etc.), or the like. The frame 422 can include rods 440a, 440b (collectively "rods 440") slidably received by receivers 450a, 450b, respectively, of the seat assembly 412. One or more pins can be removed from holes 460 to vertically move the frame 422. The pins can be inserted in the holes 460 to lock the chest support assembly 410 to the seat assembly 412.

Figure 12:
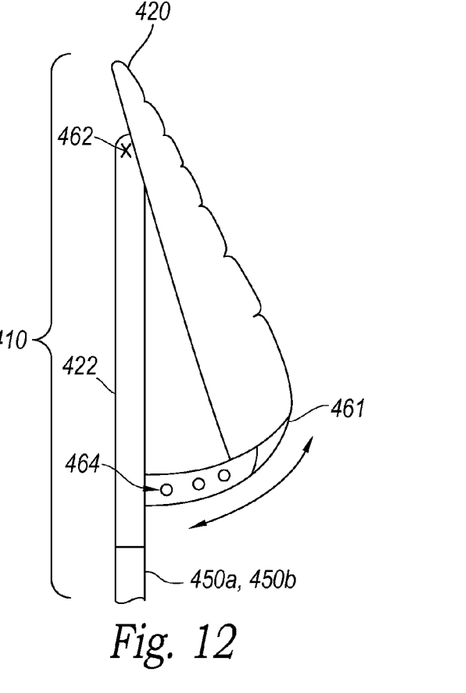
FIG. 12 is a side view of the chest support assembly of FIG. 11 with a tilted chest support.

FIG. 12 is a side view of the chest support assembly 410 of FIG. 11. A tilt mechanism 461 can allow rotation of the chest support 420 about an axis of rotation 462. A hinge (not shown in FIG. 12) can rotatably couple the chest support 420 to the frame 422. The tilt mechanism 461 can be unlocked by removing a pin, and the chest support 420 can be rotated about the axis of rotation 462. The pin can be inserted into one of the holes 464 to lock the chest support 420 at the desired angle of inclination. Other types of mechanisms (e.g., tilt mechanisms, pivot mechanisms, etc.) can be utilized.

Figure 13:
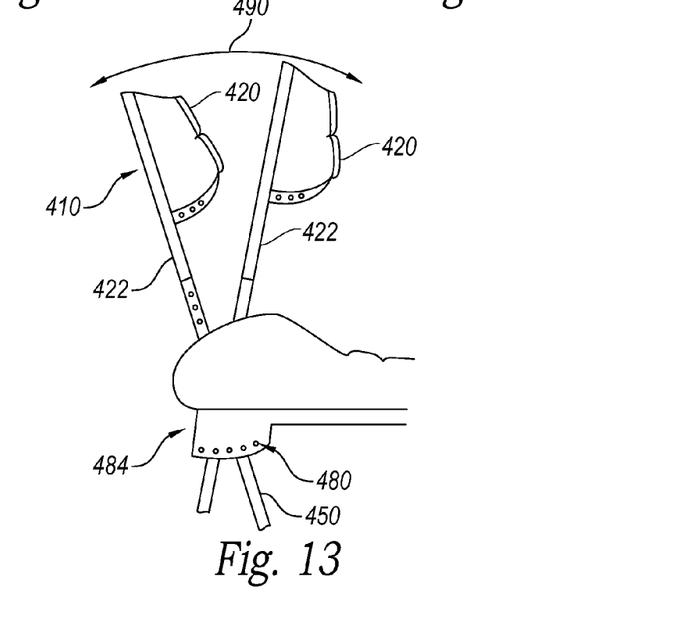
FIG. 13 is a side view of the chest support assembly of FIG. 11 in different positions.

FIG. 13 is a side view of a tilt mechanism 484 for tilting the chest support assembly 410. A pin can be removed from one of the holes 480 to rotate the frame 422, as indicated by arrow 490. When the chest support 420 is at the desired orientation, the pin can be inserted through the appropriate hole 480 to lock the chest support assembly 410.

To tattoo a lower body part (e.g., a client's leg when the client is sitting in a chair), the chest support 420 can be moved forward. Once the chest support 420 is at the desired orientation, the tilt mechanism 481 can be locked. The tattoo artist can straddle the chest support assembly 410 and can comfortably lean on the chest support 420 for a relatively long period time to work on the client's leg. Although not shown in FIGS. 11-13, armrests can be incorporated into the chest support assembly 410. For example, armrests can be rotatably coupled to the sides of the chest support 420.

Figure 14:
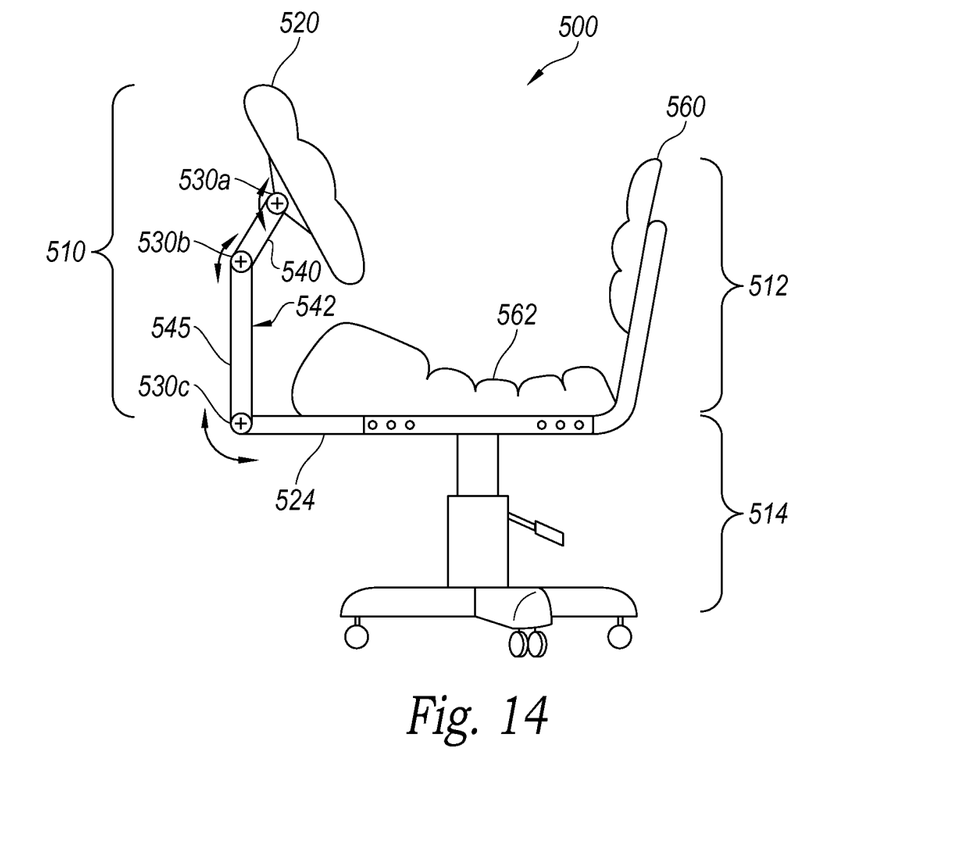
FIG. 14 is a side view of a chair in accordance with an embodiment of the present technology.

FIG. 14 is a side view of a tattoo chair 500 in accordance with an embodiment of the present technology. The tattoo chair 500 can include a chest support assembly 510, a back support assembly 512, and a seat assembly 514. The chest support assembly 510 can include a chest support 520 and a connector apparatus 542. In some embodiments, including the illustrated embodiment, the connector apparatus 542 includes members 540, 545 and pivots 530a, 530b, 530c. The elongated member 540 can extend between the pivots 530a, 530b. The elongated member 545 can extend between the pivots 530b, 530c. The back support assembly 512 can include a back support 560 for supporting the artist's back. The artist can sit on a seat 562 and either lean rearward against the back 560 or lean forward against the chest support 520.

A person receiving a tattoo can sit on the stools discussed in connection with FIGS. 1-13 or the chair discussed in connection with FIG. 14. In a single tattoo session, stools 100, 300, or 400 or chair 500 can be alternatively used by the client and the artist. The client and tattoo artists can simultaneously sit on two stools or chairs. The embodiments, features, and methods and techniques described herein may be incorporated into other types of support apparatuses (e.g., stools and chairs) used in a wide range of settings. In some embodiments, the apparatuses disclosed herein include one or more of the features, systems, devices, materials, methods and techniques described in U.S. patent application Ser. No. 12/876,953, which is incorporated herein by reference in its entirety. For example, the stools and chairs discussed herein can include hydraulics systems, hinges, locking mechanisms, or other components disclosed in U.S. patent application Ser. No. 12/876,953. In some procedures, a person receiving a tattoo can be supported by one of the apparatuses disclosed in U.S. patent application Ser. No. 12/876,953 while the tattoo artist sits on the stool 100. In addition, the embodiments, features, systems, devices, materials, methods and techniques described herein may, in certain embodiments, be applied to or used in connection with any one or more of the embodiments, features, systems, devices, materials, methods and techniques disclosed in the above-mentioned U.S. patent application Ser. No. 12/876,953.

Unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. The term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A stool, comprising:
a seat assembly; and
a chest support assembly including
a chest support having a front side and a backside, wherein the backside of the chest support is positioned to contact and support a chest of a user sitting on the seat assembly and straddling the chest support assembly while allowing movement of the user's arms on the front side of the chest support, and
at least one armrest movable relative to the chest support between an upright position and a lowered position, wherein the at least one armrest in the upright position has a support surface that is substantially flush with the backside of the chest support such that the support surface is positioned to contact and support the user's chest contacting the backside of the chest support, and wherein the support surface of the at least one armrest in the lowered position is located on the front side of the chest support to support the user's arms.

2. The stool of claim 1, wherein the support surface of the at least one armrest and a support surface of the chest support are configured to cooperate to support a generally continuous area of the user's chest facing the backside of the chest support.

3. The stool of claim 1, wherein the backside of the chest support has a generally gapless chest support surface for supporting the user's chest when the at least one armrest is in the upright position, wherein the generally gapless chest support surface includes the support surface of the at least one armrest and a surface of the chest support.

4. The stool of claim 1, wherein the least one armrest includes a first armrest and a second armrest, wherein most of the first and second armrests are positioned directly underneath laterally extending portions of the chest support when the first and second armrests are in the upright positions.

5. The stool of claim 1, wherein
the chest support is positioned to support the user's chest when the user sits on the seat assembly and straddles the chest support assembly; and
the at least one armrest in the lowered position extends away from the user's torso when the user's chest contacts the backside of the chest support, and wherein the at least one armrest in the upright position is located to contact the user's chest.

6. The stool of claim 1, wherein the chest support assembly has a generally planar configuration when the at least one armrest is in the upright position and the at least one armrest in the lowered position protrudes from the chest support.

7. The stool of claim 6, wherein the at least one armrest in the lowered position is substantially perpendicular to the chest support.

8. The stool of claim 1, wherein the at least one armrest is rotatable along an arc in a range from about 80 degrees to about 90 degrees.

9. The stool of claim 1, wherein the at least one armrest includes a first armrest and a second armrest, wherein the chest support defines first and second armrest-receiving openings that receive the first and second armrests, respectively, when the first and second armrests move from the lowered position to the upright position.

10. The stool of claim 1, wherein the chest support assembly further includes a pivoting mechanism with an unlocked state that allows the chest support to rotate relative to the seat assembly and with a locked state that prevents rotation of the chest support relative to the seat assembly.

11. A stool, comprising:
a seat assembly;
a chest support positioned to contact a user's chest when the user sits on the seat assembly and straddles the stool; and
first and second armrests movably coupled to the chest support such that support surfaces of the first and second armrests move away from the chest support and the user's torso when the first and second armrests move from raised positions toward lowered positions, wherein the support surfaces of the first and second armrests are positioned to face and lay flat along the user's torso when the first and second armrests are in the raised positions, wherein the support surfaces of the first and second armrests are positioned to support the user's arms when the first and second armrests are in the lowered positions, and wherein the support surfaces of the first and second armrests in the raised positions and a chest support surface of the chest support define a gapless surface for contacting the user's torso.

12. A stool, comprising:
a seat assembly;
a chest support positioned to contact a user's chest when the user sits on the seat assembly and straddles the stool; and
first and second armrests movably coupled to the chest support such that support surfaces of the first and second armrests move away from the chest support and the user's torso when the first and second armrests move from raised positions toward lowered positions, wherein the support surfaces of the first and second armrests are positioned to face and lay flat along the user's torso when the first and second armrests are in the raised positions, wherein the support surfaces of the first and second armrests are positioned to support the user's arms when the first and second armrests are in the lowered positions, and, wherein the support surfaces of the first and second armrests and the chest support are positioned to cooperate to support a generally continuous area of the subject's torso facing the chest support and the first and second armrests.

13. The stool of claims 11 or 12, wherein most of the first and second armrests are positioned directly underneath laterally extending portions of the chest support when the first and second armrests are in the raised positions, and wherein the laterally extending portions are positioned to contact and support the user's shoulders.

14. A stool, comprising:
a seat assembly; and
a chest support assembly including a chest support and armrests, wherein each armrest is movable between a raised position for being substantially flush with the chest support and a lowered position for supporting a user's arm located on a front side of the chest support, and wherein the chest support and the armrests are positioned to support the user's torso located on a backside of the chest support assembly when the user sits on the seat assembly and straddles the stool and when each armrest is in the raised position.

15. The stool of claim 14, wherein the backside of the chest support assembly has a generally gapless chest support surface that includes support surfaces of the armrests in the raised positions and a backside surface of the chest support.

\* \* \* \* \*